United States Patent [19]

Ghormley

[11] 4,207,888
[45] Jun. 17, 1980

[54] BAFFLE DEVICE FOR FACE TENT

[76] Inventor: Lidia S. Ghormley, P.O. Box 119, Sonora, Calif. 95370

[21] Appl. No.: 953,003

[22] Filed: Oct. 20, 1978

[51] Int. Cl.[2] .......... A61M 15/00

[52] U.S. Cl. .......... 128/203.29; 128/205.25; 128/206.24; 128/207.12

[58] Field of Search .......... 128/205, 141 R, 142.7, 128/185, 188, 193, 194, 195, 204, 205, 186, 1 B, 191 A

[56] References Cited

U.S. PATENT DOCUMENTS

| | | | |
|---|---|---|---|
| 2,508,050 | 11/1950 | Valente | 128/205 |
| 3,295,521 | 1/1967 | Balch | 128/205 |
| 3,680,557 | 8/1972 | Doniguian | 128/191 A |
| 3,821,947 | 7/1974 | Schossow | 128/194 |
| 3,894,537 | 7/1975 | Camp | 128/193 |
| 4,133,656 | 1/1979 | Kippel et al. | 128/188 X |

*Primary Examiner*—Henry J. Recla

[57] ABSTRACT

A flow baffle for use in an aerosol therapy system including a jet nebulizer device, which is connected by large bore tubing to a face tent worn by a patient, with the water aerosol and oxygen-air mixture so delivered being free to pass through and out of the face tent. The flow baffle comprises a disc covering over the face tent inlet port and retained in spaced relationship thereto by a series of vanes, which fit snugly into the inlet tube of the face tent. Stop means on the vanes limit penetration thereof into the inlet tube so that the disc remains spaced from the port opening at least a predetermined amount whereby flow into the face tent is not materially impeded and there is no back pressure build up.

2 Claims, 2 Drawing Figures

U.S. Patent  Jun. 17, 1980  4,207,888

BAFFLE DEVICE FOR FACE TENT

BACKGROUND OF THE INVENTION

Aerosol therapy is commonly prescribed for patients suffering from various respiratory ailments, such as asthma, emphysema and pneumonia. It is also a common post-operative treatment following throat surgery and for patients receiving oxygen treatment, which tends to dry out membranes. In a common aerosol therapy system a mixture of oxygen and air with water in a very fine particulate form suspended therein is discharged into a face tent which fits snugly around the cheeks and chin of the patient but is open at the top to allow free flow of aerosolized fluid therefrom. At relatively high flow rates, e.g. 30 to 40 liters of oxygen-air mixture per minute, the unrestrained aerosol fluid flows freely out of the face mask without being retained long enough to enable the patient to inhale an appreciable amount thereof. Others have attempted to slow the flow rate by applying check valves or the like, but such commonly results in a build up of back pressure. Since the ratio of air to pure oxygen is determined by the air intake opening on the jet nebulizer, as well as the flow rate of the oxygen, and increase in back pressure will back up to the air intakes to block them, thereby increasing the oxygen concentration.

OBJECTS OF THE INVENTION

It is an object of this invention to provide means for retaining the aerosol mixture suspended within the face tent to maximize the effects thereof.

It is a further object of this invention to provide means for retaining the aerosolized fluid within the face tent without altering air to oxygen ratio.

It is a further object of this invention to provide means for retarding flow of the aerosol fluid, without producing a back pressure build up in the delivery hose.

Other objects and advantages of this invention will become apparent from the description to follow, particularly when read in conjunction with the accompanying drawing.

SUMMARY OF THE INVENTION

In carrying out this invention I provide a disc which is carried generally parallel to, and spaced inward from, the inlet port in the face tent. A series of vanes, which extend from the disc, are slidably received in the inlet duct of the face tent to retain the disc in place by friction. The disc substantially covers the inlet port opening, but stop members on the vanes limit the penetration thereof into the inlet duct so that there is adequate flow area radially outward of the vanes under the disc and into the face mask, preventing a pressure build up in the delivery tube. Cross-sectional areas between the vanes and under the disc are sufficient that flow of the aerosol fluid is not materially impeded and the oxygen concentration is not altered.

DESCRIPTION OF THE PREFERRED EMBODIMENT

Figure 1:
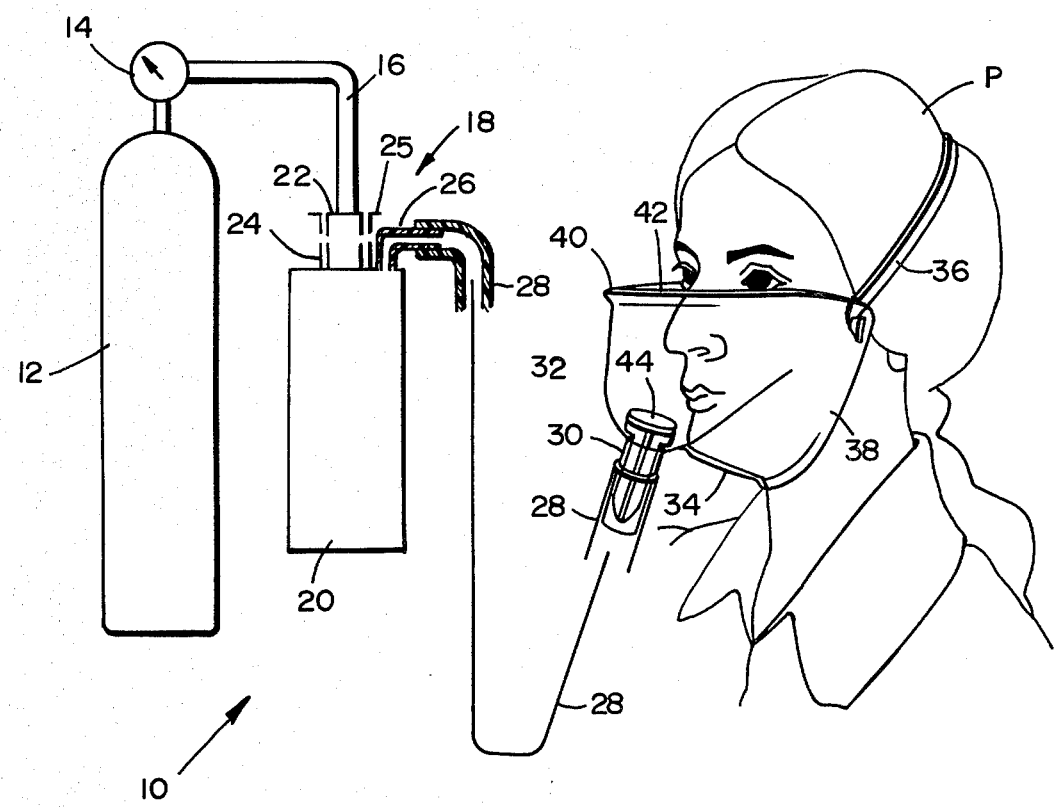
FIG. 1 is a view in perspective, partially schematic, showing an aerosol therapy system incorporating the flow baffle of this invention.
Figure 2:
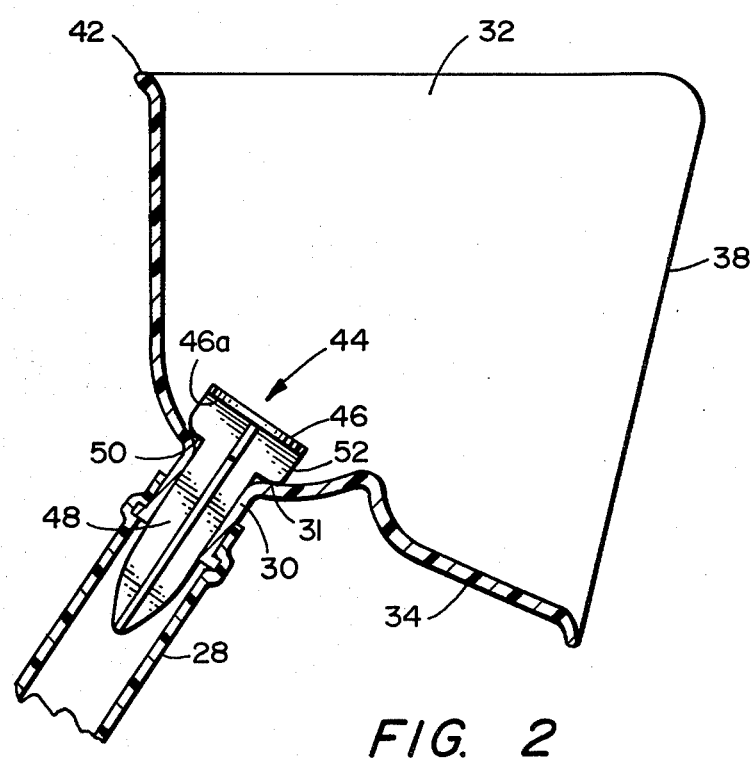
FIG. 2 is a section view through a face tent showing the flow baffle in position in the inlet tube.

Referring now to FIG. 1 with greater particularity the aerosol therapy system 10 of this invention, includes a suitable source of oxygen 12 provided with a flow meter or pressure gauge 14 and a supply duct 16 connected to a conventional jet nebulizer 18, such as that shown in U.S. Pat. No. 3,836,079. The nebulizer includes a jar 20 containing a supply of a liquid, such as water, and an adjustable mixer cap 22 carrying a valve sleeve 24 or other suitable means for adjusting the desired ratio of oxygen to air. A scale (not shown) is provided around the sleeve valve 24 so that the desired concentration of oxygen may be selected by turning the sleeve to a selected position. For example, a 40% concentration may be selected and since air contains roughly 20% oxygen, this concentration is achieved with a one to three oxygen-air ration.

The oxygen-air mixture with liquid particles entrained therein is delivered from the nozzle 26, through a large bore delivery hose to the inlet passageway 30 of a face tent 32, which is preferably formed of a soft vinyl material with a molded in chin rest 34 which fits snugly under and against the chin of the patient P. An adjustable strap 36 fits over the patient's head to hold the side edges 38 rather snugly against the patient's cheeks. A generally horizontal cross edge 40 extends across the patient's cheeks and nose but is spaced therefrom to provide ample clearance at 42 for free egress of the fluid delivered at inlet tube 30.

Since the face tent does not fit snugly across the patient's face the aerosol fluid delivered at inlet duct 30 is relatively unimpeded and tends to flow past the patient's nose without lingering long enough to enable inhalation. In a typical setting of the nebulizer 18, with a 40% mixture of oxygen, forty liters of gas (ten liters of oxygen mixed with thirty liters of air) flow per minute through the nozzle 26 into delivery tubes 28. At this relatively high rate of flow, there is virtually no aerosol mist hovering within the face tent 32.

In carrying out this invention, I provide a baffle device 44 comprising a circular disc 46 which is of diameter to completely cover the port opening 31. Extending from the disc 46 are a plurality of radial vanes or webs 48 which are of a width to fit snugly within an inlet duct 30 and be retained therein by friction. Stop shoulders 50 on the fingers limit the penetration thereof into the inlet opening 30 so that there is ample clearance at 52 to enable virtually unimpeded flow of the aerosol. The spaces between the fingers 48 as well as the clearance 52 provide ample flow capacity with no back pressure to alter the concentration of oxygen. Hence, the fluid flows upward between the fingers and out through the clearance 52 to enter radially into the face tent in all directions from under the disc 46. With flow being diverted and diffused by the undersurface 46a of the disc 46, the aerosol stream is retarded and hovers within the face tent. The result is a continuing suspension of aerosol within the face tent 32 with the resultant great increase in respiratory benefits.

While this invention has been described in conjunction with a preferred embodiment thereof, it is obvious that modifications and changes therein may be made by those skilled in the art without departing from the spirit and scope of this invention, as defined by the claims appended hereto.

Having described my invention, I claim.

1. For use in an aerosol therapy system including:
a pressurized source of oxygen;
a nebulizer device connected to said source;
a face tent adapted to be worn by a patient with sealing edges thereof held snugly against the sides of the patient's face and under the chin, and other edges thereof extending laterally across the patient's cheeks and nose but in spaced relation thereto; and
a large bore fluid inlet connection at the bottom portion of said face tent terminating at a port opening therein; and
a large bore tubing connecting said nebulizer to said face tent fluid inlet;
a flow baffle comprising;
a flow diverter in said face tent including a disc covering the port opening and spaced therefrom so that fluid flowing through said port opening is diverted radially in all directions without being materially impeded; and
holding means comprising a plurality of vanes extending normal to said disc, the outer edges of said vanes being snugly slidable received in said fluid inlet and retained in place therein by friction.

2. The flow baffle defined by claim 1 including:
stop means for limiting the penetration of said vanes into said fluid inlet.

* * * * *